United States Patent [19]

Subramanyam

[11] 4,451,450

[45] May 29, 1984

[54] CATIONIC COMPOUNDS USEFUL FOR MAKING RADIODIAGNOSTIC AGENTS

[75] Inventor: Vinayakam Subramanyam, Westwood, Mass.

[73] Assignee: New England Nuclear Corporation, Boston, Mass.

[21] Appl. No.: 311,770

[22] Filed: Oct. 15, 1981

[51] Int. Cl.³ .................... A61K 43/00; A61K 49/00; C07F 9/66; C07F 9/90

[52] U.S. Cl. ............................ 424/1.1; 260/429 R; 260/440; 260/446; 568/2; 568/8; 568/13; 568/14; 568/15; 568/16; 568/17; 424/9

[58] Field of Search ............... 260/429 R, 440, 446; 568/2, 8, 13–17; 424/1, 1.5, 9

[56] References Cited

U.S. PATENT DOCUMENTS

| | | | |
|---|---|---|---|
| 2,587,805 | 3/1952 | Akobjanoff | 260/440 |
| 3,188,345 | 6/1965 | Burg et al. | 568/2 |
| 3,478,035 | 11/1969 | Barrett | 564/19 |
| 3,478,036 | 11/1969 | Winkelmann et al. | 564/19 |
| 3,798,241 | 3/1974 | Kagan et al. | 260/446 |
| 3,819,670 | 6/1974 | Kemp | 260/440 |
| 4,133,872 | 1/1979 | Schmidt-Dunker et al. | 424/1 |
| 4,247,534 | 1/1981 | Bevan | 424/1 |
| 4,338,248 | 7/1982 | Yokoyama et al. | 424/1 |
| 4,363,793 | 12/1982 | Blau et al. | 424/1 |
| 4,374,821 | 2/1983 | Glavan et al. | 260/429 R |

FOREIGN PATENT DOCUMENTS

38756 10/1981 European Pat. Off. ................ 424/1

OTHER PUBLICATIONS

Deutsch et al., J. Nucl. Med., vol. 22, (Oct. 1981): 897–907.
Friesen, D. K. et al., J. of Molecular Structure, 31, (1976), 77–95.
Communications to the Editor, J. Am. Chem. Soc., 1980, vol. 102, No. 22, 1980, pp. 6849–6851.
Zsuzsa Nagy-Magos et al., J. of Organometallic Chemistry, 171, (1979), 97–102.
Akhtar, M. et al., Inorganic Chemistry, vol. 11, No. 12, 1972, pp. 2917–2921.
Communications to the Editor, J. Am. Soc., 101, 1979, pp. 1053–1054.
Brown, L. D. et al., Inorganic Chemistry, vol. 17, No. 3, 1978, pp. 729–734.
Albright, J. O. et al., J. Am. Chem. Soc., 101, (1979), pp. 611–619.
Kyba, E. P. et al., J. Am. Chem. Soc., vol. 102, No. 23, 1980, pp. 7012–7014.
Butter, S. A. et al., J. Am. Chem. Soc., (1970), pp. 1411–1415.
Inoue, Y. et al., Bulletin of the Chem. Soc. of Japan, vol. 51(B), (1978), pp. 2375–2378.
Chatt, J. et al., J. Chem. Soc., (1961), pp. 896–904.
Mazzi, U. et al., Inorganic Chemistry, vol. 16, No. 5, 1977, pp. 1042–1048.
Chatt, J. et al., J. Chem. Soc., (1962), pp. 2545–2549.

Ferguson, J. E. et al., Aust. J. Chem., 1970, 23, 453–61.
King, R. B., Acc. Chem. Res. 1980, 13, pp. 243–248.
Wymore, C. E. et al., J. Inorg. Nucl. Chem., 1960, vol. 14, pp. 42–54.
Ferguson, J. E. et al., J. Inorg. Nucl. Chem., 1966, vol. 28, pp. 2293–2296.
Cooper, P. et al., J. Chem. Soc., (C), (1971), pp. 3031–3035.
Subramanian, Gopal et al., Proceedings of the 28th Annual Meeting, Los Vegas, Jun. 16–19, 1981, vol. 22, No. 6, p. 51.
Deutsch, E. et al., Science, vol. 214, (1981), pp. 85–86.
Ferguson, J. E. et al., Chemistry and Industry, Nov. 22, 1958, p. 1555.
Curtis, N. F., Chemistry and Industry, May 24, 1958, pp. 625–626.
Communications to the Editor, J. Am. Chem. Soc., 97, (1975), pp. 1955–1956.
Bandoli, G. et al., J.C.S. Dalton, (1976), pp. 125–130.
Viard, B., J. Inorg. Nucl. Chem., 1977, vol. 39, pp. 1090–1092.
Fergusson et al., Chemistry and Industry, pp. 347, 348.

*Primary Examiner*—Christine M. Nucker
*Attorney, Agent, or Firm*—Sewall P. Bronstein; George W. Neuner

[57] ABSTRACT

A normally solid, hydrophilic compound capable of binding with Tc-99m to form a cationic complex is provided. The compound has a formula selected from:

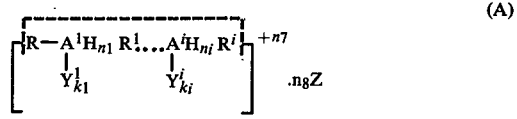

(A)

or

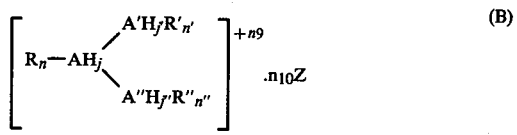

(B)

wherein:

$R$, $R'$, $R''$, $R^1$, $R^2$, $R^3$, $R^4$, $R^5$ and $R^6$ are each independently selected from hydrogen; or substituted or unsubstituted alkyl, alkylene, aryl, alkylaryl, arylalkyl, monocycloalkyl, polycycloalkyl, heterocyclic and carbocyclic groups; and $R$ plus $R^i$ in formula (A) may be taken together to form a cyclic compound;

$A$, $A'$, $A''$, $A^1$, $A^2$, $A^3$, $A^4$, $A^5$ and $A^6$ are independently neutral functional elements, each having a free electron pair available for accepting a proton to provide a charged ligand and having the capability of complexing with Tc-99m to form a cationic complex;

$Y^1$, $Y^2$, $Y^3$, $Y^4$, $Y^5$ and $Y^6$ are each independently selected from hydrogen; or substituted or unsubstituted alkyl, alkylene, aryl, alkylaryl, arylalkyl, monocycloalkyl, polycycloalkyl, heterocyclic and carbocyclin groups;

Z is an anion;
i is an integer from 0 to 6;
j, j' and j" are each independently 0 or 1;
$k^1$, $k^2$, $k^3$, $k^4$, $k^5$ and $k^6$ are each independently 0 or 1;
n, n' and n" are each independently the integer 1 or 2;
$n_1$, $n_2$, $n_3$, $n_4$, $n_5$, $n_6$, are independently 0 or 1; and
$n_7$ and $n_8$ are each an integer from 1 to 6; and $n_9$ and $n_{10}$ are each an integer from 1 to 3.

These compounds are capable of reducing technetium to form stable cationic complexes. Radiolabelled such complexes are useful in connection with radiodiagnostic test of myocardial and/or hepatobiliary tissues.

36 Claims, No Drawings

CATIONIC COMPOUNDS USEFUL FOR MAKING RADIODIAGNOSTIC AGENTS

FIELD OF THE INVENTION

The present invention relates to cationic radiodiagnostic agents and, in particular, to water soluble cationic ligands useful as intermediates for producing $^{99m}$Tc-labelled cationic radiodiagnostic agents, novel $^{99m}$Tc-labelled cationic radiodiagnostic agents, kits for preparing such $^{99m}$Tc-labelled cationic radiodiagnostic agents, and methods for using such $^{99m}$Tc-labelled cationic radiodiagnostic agents.

BACKGROUND OF THE INVENTION

Various complexes of monodentate and bidentate ligands with technetium have been made and studied. These complexes generally were made for use in studies to determine the various oxidation states of technetium and for other research regarding the structure of such complexes and metal-coordination chemistry. Such studies have been reported in, for instance, *Chemistry and Industry*, pp. 347–8 (Mar. 26, 1960); *J. Inorg. Nucl. Chem.*, Vol. 28, pp 2293–96 (1966); *Aust. J. Chem.*, 23, pp 453–61 (1970); *Inorganic Chem.*, Vol. 16, No. 5, pp. 1041–48 (1977); *J. Inorg. Nucl. Chem.*, Vol. 39, pp. 1090–92 (1977); and *J. C. S. Dalton*, pp. 125–30 (1976).

Recently, in a presentation to the American Pharmaceutical Association, E. A. Deutsch disclosed that certain complexes of DIARS, i.e.

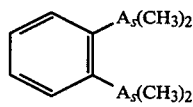

I and Tc-99m, and certain complexes of DMPE, i.e. $(CH_3)_2 PCH_2CH_2P(CH_3)_2$ and Tc-99m, may be useful as radiodiagnostic agents for myocardial or hepatobiliary imaging. $[^{99m}Tc\text{-}(DMPE)_2Cl_2]^+$ and $[^{99m}Tc\text{-}(DIARS)_2 Br_2]^+$ were prepared by Deutsch by heating in an open flask a reaction mixture containing the appropriate hydrogen halide in aqueous alcohol solution, $^{99m}$Tc-sodium pertechnetate, and ortho-phenylenebis(dimethylarsine), i.e. DIARS, or bis-(1,2-dimethylphosphino)ethane, i.e. DMPE. The reaction was reported to take about 30 minutes. The labelled complex was then purified by chromatographic methods involving ion exchange columns.

The labelled complex produced according to the procedure of Deutsch has several practical disadvantages. The procedure requires handling several ingredients including an organic solvent to make the reaction mixture and then purifying the resulting radiolabelled complex by chromatography. Each of these handling steps can contaminate the system and final product. The purification step further requires additional time for preparation of the final product. These steps require a skilled technician and are performed at the site of use, just prior to use. Thus, a complex, time consuming chemical preparation is required during which sterility of ingredients and containers is difficult to maintain. Thus, to assure freedom from contamination, a final sterilization step is required, which further adds to preparation time. Because Tc-99m has a short half-life, lengthy preparation methods are undesirable. Thus, the complexity of the preparation, both with regard to maintaining sterile conditions and to purification of the $^{99m}$Tc-labelled complex make the Deutsch procedure undesirable.

It would be highly desirable to have a sterilized kit with all the necessary materials prepared by the manufacturer, to which only the Tc-99m need be added at the site of use to produce the desired labelled complex directly in high enough yield to obviate the need for purification. It would also be desirable for the kit materials to be in a closed container or vial, pre-sterilized, so that the only step to be performed at the site of use would be the addition of the radionuclide. To increase stability and shelf-life of the kit, it would be highly desirable that the materials be readily lyophilized, preferably from an aqueous solution.

By achieving the desirable features outlined above, a convenient-to-use heart imaging radiopharmaceutical agent would be provided that is capable of concentrating in healthy heart tissue to provide a negative image of an infarct, damaged or ischemic tissue.

SUMMARY OF THE INVENTION

The present invention provides an acid salt of a mono or polydentate ligand that is water soluble, stable in a lyophilized state, and is capable of binding with Tc-99m to form a cationic complex. The acid salt may be generally represented by the formula:

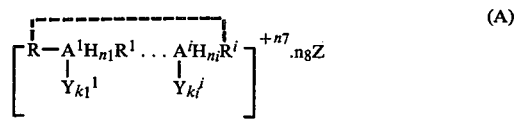

(A)

wherein:

i is an integer from 0 to 6;

R, $R^1$, $R^2$, $R^3$, $R^4$, $R^5$ and $R^6$ are each independently selected from hydrogen or substituted or unsubstituted alkyl, aryl, alkylaryl, arylalkyl, monocycloalkyl, polycycloalkyl, heterocyclic and carbocyclic groups, and R plus $R^i$ may be taken together to form a cyclic compound or separately to form a linear compound;

$Y^1$, $Y^2$, $Y^3$, $Y^4$, $Y^5$ and $Y^6$ are independently selected from substituted or unsubstituted alkyl, aryl, alkylaryl, arylalkyl, monocycloalkyl, polycycloalkyl, heterocyclic and carbocyclic groups;

$A^1$, $A^2$, $A^3$, $A_4$, $A^5$ and $A^6$ are the same or different neutral donor atoms, each having a free-electron pair available for accepting a proton to provide a charged ligand or for complexing with Tc-99m or Tc-99 to form a cationic complex;

Z is preferably a parenterally acceptable anion;

$k_1$, $k_2$, $k_3$, $k_4$, $k_5$ and $k_6$ are each independently zero or one;

$n_1$, $n_2$, $n_3$, $n_4$, $n_5$ and $n_6$ are independently 0 or 1; and $n_7$ and $n_8$ are integers from 1 to 6 where $$n_7 = \sum_{i=1}^{6} n_i$$

and the charge represented by $n_8Z$ is equal in magnitude and opposite in sign to $+n_7$ or

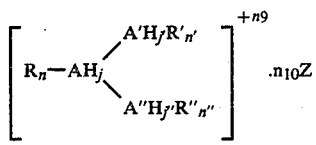
.n₁₀Z    (B)

wherein:
R, R' and R" are independently selected from hydrogen or substituted or unsubstituted alkyl, aryl, alkylaryl, arylalkyl, monocylcloalkyl, polycycloalkyl, heterocyclic and carbocyclic groups;
A, A' and A" are independently selected from the group of neutral donor atoms having a pair of electrons available for accepting a proton to provide a charged ligand or for complexing with Tc-99m or Tc-99 to form a cationic complex;
j, j' and j" are independently 0 or 1;
n, n' and n" are independently the integer 1 or 2;
Z is the same as defined above; and
$n_9$ and $n_{10}$ are integers selected from 1 to about 3; where $n_9 = j + j' + j''$ and the charge represented by $n_{10}Z$ is equal in magnitude and opposite in sign to $+n_9$.

The acid salts of the present invention having the above formula are normally solid compounds, water-soluble, readily lyophilized, and capable of reducing pertechnetate and binding with technetium to form stable cationic complexes. For purposes of this invention a "stable cationic complex" means a cationic complex that has a sufficiently long life to administer it as a radiopharmaceutical and obtain the desired radioscintigraphic image.

The R's in formulas (A) and (B) are preferably alkyl radicals having 1 to 6 carbon atoms such as methyl, ethyl, etc., and the like, and aryl radicals such as benzyl, phenyl, etc., and the like. The novel ligand acid salts of the present invention are useful for preparing radiopharmaceutical compositions containing cationic complexes of Tc-99m. Such cationic technetium-labelled complexes are useful for radiodiagnostic tests in connection with myocardial or hepatobiliary tissues.

The useful cationic Tc-99m complexes are made by reacting the novel ligand acid salts of this invention with $^{99m}$Tc-pertechnetate in the presence of a suitable complex formation assisting anion. In one embodiment, the reaction is carried out in the presence of halide ions, and of these the chloride is most preferred. In another embodiment, the reaction is carried out in the presence of pseudo-halogen anions, and of these the reaction product with thiocyanate ion is particularly useful. In yet another embodiment, the reaction is carried out in the presence of hydroxide anions.

DETAILED DESCRIPTION OF THE INVENTION

The water-soluble ligand acid salts of the present invention can be prepared from a wide variety of monodentate and polydentate ligands. Typical examples of such ligands include, for instance, aryl compounds having arsenic, phosphorus, nitrogen, sulfur, oxygen, selenium, tellurium, or any combination of them, substituted ortho to each other. For example, o-phenylene compounds having the structure:

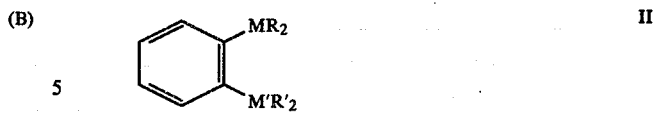

in which M and M' are arsenic, phosphorus, nitrogen, sulfur, oxygen, selenium, tellurium, or any combination of them, and R and R' are independently hydrogen, or an organic group, preferably an alkyl group having 1 to 6 carbon atoms, an aryl group such as phenyl, or the like, and substituted such groups. Additional examples of suitable ligands include bidentate cis-tetraethylene ligands of the formula:

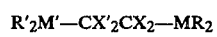

$$R'_2M'-CX'_2CX_2-MR_2 \qquad III$$

in which M, M', R, and R' are as defined above and X and X' are independently selected from hydrogen, halide, or substituted or unsubstituted lower alkyl groups having 1 to about 6 carbon atoms. Further examples of suitable ligands include those having the formula:

where M, M', R, and R', are as defined above, M" is independently selected from arsenic, phosphorous, nitrogen, sulfur, oxygen, selenium, and tellurium, and R" is independently selected from hydrogen, halide or an organic radical, preferably an alkyl radical having 1 to about 6 carbon atoms, an aryl radical such as phenyl, or the like, and substituted such groups.

Particularly preferred ligands for the practice of this invention are the bis-dialkylphosphinoethanes and their substituted derivatives, including, for example,
1,2-bis(dimethylphosphino)ethane,
1,2-bis(di(trifluoromethyl)phosphino)ethane,
1,2-bis(dimethylphosphino)-1,1-difluoroethane,
1,2-bis(dimethylphosphino)-1-fluoroethane,
1,2-bis(dimethylphosphino)propane,
1,2-bis(di(trifluoromethyl)phosphino)-1,1,2,2-tetrafluoroethane,
1,2-bis(di(trifluoromethyl)phosphino)propane,
2,3-bis(di(trifluoromethyl)phosphino)butane,
1,2-bis(di(trifluoromethyl)phosphino)butane,
1,3-bis(dimethylphosphino)butane,
1,3-bis(dimethylphosphino)propane,
1,3-bis(di(trifluoromethyl)phosphino)propane,
1,2-bis(dimethylphosphino)-1,1-dichloro-2,2-difluoroethane, and similar compounds wherein the phosphorus is replaced by nitrogen, arsenic, sulfur, oxygen, selenium, tellurium, or another atom having a free electron pair, and the like.

Other useful ligands include the alkylaminobis(difluorophosphine), i.e., $RN(PF_2)_2$, ligands and the like where R is an organic group, preferably an alkyl group having 1 to about 6 carbon atoms, an aryl group as phenyl, or the like, and substituted such groups; and the o-phenylene compounds such as, for example, orthophenylenebis(diarsine), orthophenylenebis(dimethylarsine), orthophenylenebis(diamine), orthophenylenebis(dimethylamine), orthophenylenebis(diphosphine), orthophenylenebis(dimethylphosphine), and the like.

Additional ligands suitable for use in the present invention are those described by Nozzo et al., in *J. Amer. Chem. Soc.*, 101, p. 3683 (1979) and by Wilson et al., *J. Amer. Chem. Soc.*, 100, p. 2269 (1978), which are hereby incorporated by reference.

Any donor element can be used in the ligand in accord with this invention provided that it is a neutral donor atom having a free-electron pair available for accepting a proton to provide a charged ligand and further provided that it has the capability of complexing with technetium (Tc-99 or Tc-99m) to form a cationic complex in the presence of suitable anions. Suitable such elements include, for instance, phosphorus (P), arsenic (As), nitrogen (N), oxygen (O), sulfur (S), antimony (Sb), selenium (Se), tellurium (Te), and the like. Preferred elements are P and As.

The acid salt of the ligand is prepared by mixing the ligand with an acid preferably having a parenterally acceptable hydrophilic anion and able to protonate the ligand in a suitable solvent. After evaporation of the solvent, the ligand acid salt is purified by recrystallization from the same solvent or another convenient solvent.

Any acid having a hydrophilic anion and capable of protonating the ligand can be used to produce the ligand acid salt. Preferably, such acids have an oxygen containing hydrophillic anion. Examples of such acids suitable for the practice of this invention include, for instance, sulfuric acid, nitric acid, phosphoric acid, tetrafluoroboric acid, oxalic acid, trichloroacetic acid, perchloric acid, hexafluorophosphonic acid, and the like. For use in humans, toxicologically acceptable acids, i.e. acids comprising toxicologically acceptable anions, are preferred.

The cationic technetium complexes useful for radiodiagnostic treatments are prepared by mixing in an aqueous or alcoholic solution the ligand acid salt and $^{99m}$Tc-pertechnetate in the presence of a suitable complex formation assisting anion and heating the mixture to form the cationic complex. Suitable complex formation assisting anions include, for instance, halide ions; pseudo-halogen ions such as the thiocyanato- ion, cyano- ion, cyanato- ion, selenocyanato- ion, fulminato-ion, and the iso-forms of these ions, and the azido- ions; hydroxide ions; and the like; which aid technetium in achieving a stable complex with the particular ligand. Preferably, the ligand acid salt is lyophilized and is contained in a sealed, sterilized vial prior to adding the pertechnetate. The pertechnetate solution can then be injected into the vial under aseptic conditions to maintain sterility. The vial is generally heated and maintained at an elevated temperature for sufficient time to form a complex of the ligand with technetium. The vial should be heated to at least 80° C. for about 30 minutes or more. Preferably, the vial is heated to 100° C. or more, and more preferably to a temperature in the range of from about 130° C. to about 150° C. At about 150° C., the reaction can be completed in about five to ten minutes, depending upon the choice and concentrations of the reactants.

It has been found that kits for the preparation of the cationic technetium complex are improved by the addition of a polyhydroxy-compound to the reaction mixture. The use of the polyhydroxy-compound, for reasons not fully understood, results in a more consistent yield of the cationic technetium complex. Preferred polyhydroxy-compounds include, for example, Hetastarch (hydroxyethyl starch), mannitol, glycerol, D-mannose, sorbitol, and the like.

The ligand acid salt of the present invention is preferably supplied in a radiopharmaceutical preparation kit comprising a sterilized unit (or multiple) dose vial containing the purified ligand acid salt. About 50 mCi of $^{99m}$Tc-pertechetate in saline is injected aseptically into the vial and the mixture heated to form the labelled cationic complex. After cooling, the resulting radiopharmaceutical preparation may be adjusted for pH and is ready for use. Typically, when the pH is adjusted, it is adjusted into the range of from about 4.0 to about 9.0, and preferably to physiological pH.

The kit preferably comprises a vial containing a lyophilized mixture obtained from an aqueous solution of the ligand acid salt, a polyhydroxy-compound, and an acid or buffer to control the pH. Preferably the pH is in the range of from about 1.0 to about 3.0, and more preferably in the range of about 1.5 to about 2.5, when using halide anions. The most desirable pH will, of course, vary depending upon the particular ligand and salt thereof being used, the anion, and upon their concentrations. For instance, when it is desired to form the cationic technetium complex in the presence of hydroxide ions as the anion, a pH greater than 9.0 is desirable. A halide or other salt can also be added to the solution to be lyophilized.

To image the heart of a mammal, in-vivo, a radiopharmaceutical preparation in accord with the invention, having a suitable quantity of radioactivity for the particular mammal, is injected intravenously into the mammal. The mammal is positioned under a scintillation camera in such a way that the heart is covered by the field of view. High quality images of the heart are obtained analogous to those seen in clinical studies using Thallium-201.

In order to obtain high quality images the yield of radioactive labelled cationic technetium complex should preferably be greater than 70% after reconstituting the lyophilized mixture and labelling. Lower yields will result in poorer image quality and undesirable purification steps will be required to produce high quality images.

This invention will be further illustrated by the examples that follow:

EXAMPLE 1

Preparation of 1,2-Bis(dimethylphosphino)ethane bis(tetrafluoroborate), i.e. $(DMPEH)_2^{2+} + .2BF_4^-$ Place 210 mg of bis(dimethylphosphino)ethane in a 50 ml round-bottomed flask maintained under a nitrogen atmosphere, and dissolve it in 10 ml of ethanol. Add 0.5 ml of a 49% solution of tetrafluoroboric acid. After 15 minutes, remove the solvent in a rotary evaporator and recrystallize the product from 15 ml of ethanol. Filter and dry under vacuum. 406 mg of a crystalline solid is obtained, which melts at 199.5°–210° C.

EXAMPLE 2

Preparation of 1,2-Bis(dimethylphosphino)ethane bis-bisulfate, i.e., $DMPEH_2^{2+} + .2HSO_4^-$ or $DMPE.2H_2SO_4$ Dissolve 470 mg of DMPE in 10 ml of ethanol in a 50 ml round-bottomed flask maintained under a nitrogen atmosphere. From a glass syringe, add, with stirring, 0.34 ml of concentrated sulfuric acid. After 10 minutes, filter the precipitate and recrystallize it from 10 ml of methanol. Filter and dry under vacuum. 920 mg of a crystalline solid is obtained, which melts at 135°–136.5° C. Structure and purity of the compound was confirmed by its infra-red and nuclear magnetic resonance spectra and elemental analysis.

EXAMPLE 3

Propylene glycol-DMPE.2H$_2$SO$_4$ Kit

Prepare a solution of 80.5 mg of DMPE-bis(bisulfate) and 525 mg sodium chloride in 26.25 ml distilled water. Add 43.75 ml of propane-1,2-diol to it with stirring, followed by 0.4 ml of 2 N hydrochloric acid to adjust the pH from 2.46 to 1.92. Dispense 2 ml of this bulk preparation into each of 30 10-cc vials. Purge each vial with a steady stream of nitrogen gas for 20 seconds and crimp seal using a teflon-coated stopper. Inject 0.5 ml physiological saline containing approximately 10 mCi $^{99m}$Tc-pertechnetate into the vial and place it in a steam autoclave preheated to 100° C. Set the temperature control to 135° C. and when that temperature is reached, maintain it for 15 minutes. Allow the system to cool to 100° C. and remove the vial from the autoclave. Evaluation by thin layer chromatography (TLC) shows that greater than 95% of the radioactivity is in the form of [$^{99m}$TcCl$_2$(DMPE)$_2$]+, the structure and charge of the complex having been confirmed by elemental analysis, infra-red and nuclear magnetic resonance spectra of the Tc-99 analogue, by electrophoretic mobility and high performance liquid chromatographic analysis (HPLC).

EXAMPLE 4

Ethanol-DMPE Kit (Prior Art)

Prepare a saturated solution of sodium chloride in ethanol by dissolving 117 mg of sodium chloride in 20 ml of degassed ethanol. Add 11.1 μl of liquid DMPE to this solution and adjust its pH to approximately 2.25 by adding concentrated hydrochloric acid. Dispense 5 ml into a 10 cc vial and crimp seal it using a teflon-coated stopper. Inject approximately 5 mCi of $^{99m}$Tc-pertechnetate eluate into the vial and place it in a boiling water bath for 1 hour. HPLC analysis shows a yield of greater than 80% of the [$^{99m}$TcCl$_2$(DMPE)$_2$]+ complex.

EXAMPLE 5

Mannitol-DMPE.2H$_2$SO$_4$ Kit

Dissolve 1 g mannitol, 150 mg sodium chloride, and 46 mg DMPE-bis(bisulfate) in 10 ml deoxygenated physiological saline solution [0.15 Molar]. Adjust the pH of the solution to 1.4 by adding the required volume of 2 N hydrochloric acid. Dispense 1 ml of the solution into each of several 10 cc vials, flushing each with nitrogen gas for 20 seconds, closing with a teflon-coated stopper and crimp-sealing it.

Labelling Procedure A

Inject 50 mCi of $^{99m}$Tc-pertechnetate in 0.5 ml physiological saline into each of several vials and place them in an oil bath, preheated and maintained at 150°±5° C., for 5–10 minutes. HPLC analyses, as in Example 4, show yields of 90 to 100%.

Labelling Procedure B

Inject 50 mCi of $^{99m}$Tc-pertechnetate in 0.5 ml physiological saline into each of several vials and place them in a steam autoclave preheated to 100° C. Set the temperature control to 135° C., and when that temperature is achieved, maintain it for 20 minutes. Allow the system to cool to 100° C. and remove the vials. HPLC analyses, as in Example 4, show yields of 95 to 100%.

EXAMPLE 6

Mannitol-DMPE.2H$_2$SO$_4$ Kit

Dissolve 5 g mannitol and 230 mg DMPE-bis(bisulfate) in about 35 ml low-oxygen distilled water, and adjust the pH of the solution to 1.0 with 3 N sulfuric acid. Under cover of nitrogen, and with stirring, add low-oxygen distilled water gravimetrically, to a solution weight of 50 g. Dispense 1 ml of this solution into each of several 10 cc vials. Freeze-dry in keeping with procedures well-known to those skilled in the art, stoppering under nitrogen. Reconstitute each vial with 1 ml of physiological saline containing about 10–20 mCi $^{99m}$Tc-pertechnetate. Utilizing techniques similar to those of Example 3, autoclave for 30 minutes at 135° C. TLC analyses, as in Example 3, show yields consistently greater than 95%.

EXAMPLE 7

Glucoheptanoic acid-DMPE.2H$_2$SO$_4$ Kit

Dissolve 115 mg DMPE-bis(bisulfate) and 4.35 grams glucoheptanoic acid in 45 ml deoxygenated physiological saline. Prepare kits by dispensing 2 mls. of this bulk solution into each of several 10 cc vials; close under nitrogen with teflon-coated stoppers and crimp-seal them. Inject 0.5 ml. of physiological saline containing approximately 5–10 mCi $^{99m}$Tc-pertechnetate and heat for 6 minutes in an oil bath pre-heated and maintained at 1150° C. Yield of [$^{99m}$TcCl$_2$(DMPE)$_2$]+ based on TLC analysis as in Example 3 is >90%.

EXAMPLE 8

DMPE.2H$_2$SO$_4$-Sodium Chloride Kits

Dissolve 0.439 g of sodium chloride in 45 ml 2 N sodium hydroxide solution and adjust the pH to 1.6 using concentrated hydrochloric acid. Add 115 mg bis(dimethylphosphino)ethane-bis-bisulfate, prepared as in Example 2, to the above solution, and dissolve it by stirring. Prepare several kits by dispensing 2 ml into each of several 10 cc vials, closing them under nitrogen with teflon-coated stoppers and crimp-sealing them. Inject 0.5 ml of normal physiological saline solution containing 5.10 mCi $^{99m}$Tc-pertechnetate into each kit and heat in an oil bath, pre-heated and maintained at 150° C., for 6 minutes. The yield of [$^{99m}$TcCl$_2$(DMPE)$_2$]+ (based upon HPLC) is greater than 90%.

EXAMPLE 9

Sucrose-DMPE.2H$_2$SO$_4$ Kit

Dissolve 4.6 mg of bis(dimethylphosphino)ethane-bis-bisulfate, prepared as in Example 2, and 430 mg sucrose in 2 ml physiological saline solution, adjust to pH 1.81 with hydrochloric acid. Close under nitrogen with a teflon-coated stopper, and crimp-seal. Inject 0.5 ml physiological saline containing 5–10 mCi $^{99m}$Tc-pertechnetate eluate.

(a) After autoclaving for 20 minutes at 135° C., the yield of [$^{99m}$TcCl$_2$(DMPE)$_2$]+ based upon TLC analysis as in Example 3, is 44%.

(b) With extended autoclaving, the yield of [$^{99m}$TcCl$_2$(DMPE)$_2$]+ can be increased to at least 80%.

EXAMPLE 10

Sorbitol-DMPE.2H$_2$SO$_4$ Kit

Dissolve 4.6 mg of bis(dimethylphosphino)ethane-bis-bisulfate, prepared as in Example 2, and 200 mg sorbitol in 2 ml physiological saline; adjust to pH 1.81 with hydrochloric acid. Close under nitrogen with a teflon-coated stopper, and crimp-seal. Add 0.5 ml physiological saline containing 5–10 mCi $^{99m}$Tc-pertechnetate eluate. After autoclaving for 20 minutes at 135° C., the conversion to [$^{99m}$TcCl$_2$(DMPE)$_2$]$^+$ is greater than 95%, by TLC analysis as in Example 3.

EXAMPLE 11

Glycerol-DMPE.2H$_2$SO$_4$ Kit

Duplicate the procedure of Example 10 in every respect but the following: substitute glycerol for sorbitol. As in Example 10, the conversion to [$^{99m}$TcCl$_2$(DMPE)$_2$]$^+$ is greater than 95%, by TLC analysis as in Example 3.

EXAMPLE 12

Mannose-DMPE.2H$_2$SO$_4$ Kit

Duplicate the procedure of Example 10 in every respect but the following: substitute mannose for sorbitol. As in Example 10, the conversion to [$^{99m}$TcCl$_2$(DMPE)$_2$]$^+$ is greater than 95%, by TLC analysis as in Example 3.

EXAMPLE 13

Hydroxyethyl Starch-DMPE.2H$_2$SO$_4$ Kit

Duplicate the procedure of Example 10 in every respect but the following: substitute 600 μl Volex ® (hydroxyethyl starch, 6% (W/V) in physiological saline, available from McGaw Laboratories) for sorbitol. As in Example 10, the conversion to [$^{99m}$TcCl$_2$(DMPE)$_2$]$^+$ is greater than 95%, by TLC analysis as in Example 3.

EXAMPLE 14

Mannitol-DMPE.2H$_2$SO$_4$ (Lyophilized Kit): [$^{99m}$Tc-(DMPE)$_3$]$^+$ Complex Formation Dissolve 5 g mannitol and 115 mg DMPE-bis(bisulfate) in about 35 ml low-oxygen distilled water, and adjust the pH to 1.0 with 3 N sulphuric acid. Under cover of nitrogen and with stirring add low-oxygen distilled water gravimetrically to a solution weight of 50 g. Dispense 1 ml of this solution into each of several 10 cc vials. Freeze-dry in keeping with procedures well-known to those skilled in the art, stoppering under nitrogen. Reconstitute each of the vials with 1 ml of physiological saline containing about 10–20 mCi of $^{99m}$Tc-pertechnetate, and add 0.15 ml 1 N sodium hydroxide solution. The pH is about 12. Utilizing techniques similar to those of Example 3, autoclave for 30 minutes at 135° C. TLC analyses show almost 95% yield of [$^{99m}$Tc(DMPE)$_3$]$^+$, the structure and charge of the complex having been confirmed by elemental analysis, infra-red and nuclear magnetic resonance spectra of the Tc-99 analogue, and by electrophoretic mobility.

EXAMPLE 15

Preparation of $^{99m}$Tc-Thiocyanato-DMPE Complexes (a) To a $^{99m}$Tc-labelled preparation of Example 6 is added 0.3 ml 0.5 N sodium hydroxide containing 25 mg potassium thiocyanate. After heating for 30 minutes in a boiling water bath, HPLC analyses shows a labelled complex distinguishable from the products of Example 5 and Example 14, but which has similar cationic characteristics by electrophoresis.

(b) To the freeze-dried (but not as yet labelled) preparation of Example 6 is added 1 ml of physiological saline containing 10–20 mCi $^{99m}$Tc-pertechnetate and 0.3 ml 0.5 N sodium hydroxide containing 25 mg potassium thiocyanate. After autoclaving for 30 minutes at 135° C. as in Example 6, HPLC analysis reveals a labelled complex distinguishable from the products of Examples 5, 14 or 15a, but which has similar cationic characteristics by electrophoresis.

EXAMPLE 16

Imaging of Rabbit Heart Using Tl-201 (Prior Art)

2 mCi of Thallium-201 (as thallous chloride in physiological saline containing 0.9% benzyl alcohol) is injected intravenously into a 2.5 Kg male New Zealand Albino rabbit. The rabbit is positioned under a Searle Pho-Gamma scintillation camera in such a way that the heart and lung area are covered by the field of view. Approximately 10 minutes after injection, sufficient counts are accumulated to produce an image of the heart analogous to that seen in clinical studies of humans.

EXAMPLE 17

Imaging of Rabbit Heart Using $^{99m}$Tc-labelled Products with $\geq$80% Yield of Desired Labelled Complex Greater than 1 mCi of the $^{99m}$Tc-labelled product of Example 3 is injected into a rabbit and imaged as in Example 16. The quality and appearance of the heart image is similar to that obtained in Example 16.

The product of any one of Examples 4, 5, 6, 7, 8, 9b, 10, 11, 12, 13 or 14 produces similar results when injected into a rabbit as described above.

EXAMPLE 18

Imaging of Baboon Heart Using $^{99m}$Tc-labelled Products with $\geq$80% of Desired Labelled Complex Greater than 10 mCi of any one of the $^{99m}$Tc-labelled products of Example 17 is injected intravenously into an adult baboon positioned under a scintillation camera as was the rabbit in Example 17. Excellent quality images of the heart are obtained, which are equivalent to those characteristically obtained with Tl-201 in humans.

EXAMPLE 19

Visualization of Hepatobiliary Transit with $^{99m}$Tc-labelled Disofenin (Prior Art)

A lyophylized vial of HEPATOLITE TM (New England Nuclear Corporation's brand of Technetium Tc99m Disofenin) is labelled with $^{99m}$Tc-pertechnetate in accordance with manufacturer's directions. At least 1 mCi of the labelled preparation is injected intravenously into a 2.5 Kg male New Zealand Albino rabbit. The rabbit is positioned under a Searle Pho-Gamma scintillation camera in such a way that the liver and gastro-intestinal tract are within the field of view. Sequential images taken from the time of injection demonstrate an initial liver uptake with gradual visualization of the gall bladder and gastro-intestinal tract, analogous to the diagnostically efficacious results obtained in clinical studies of normal healthy humans.

EXAMPLE 20

Visualization of Hepatobiliary Transit with $^{99m}$Tc-Thiocyanato-DMPE Complexes Greater than 1 mCi of the $^{99m}$Tc-Thiocyanato-DMPE complex from either Example 15a or 15b is injected into a rabbit as in Example 19. Sequential images of hepatobiliary transit reveal at least as rapid passage as that in Example 19, with comparable image quality of the liver, gall bladder and gastro-intestinal tract.

This invention has been described in detail with particular reference to the preferred embodiments thereof. However, it will be appreciated that those skilled in the art, upon reading this disclosure, may make modifications and improvements within the spirit and scope of the invention.

I claim:

1. A normally solid, hydrophilic compound capable of binding with Tc-99m to form a cationic complex and having a formula selected from:

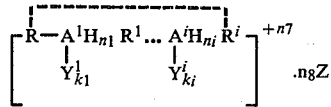
(A)

or

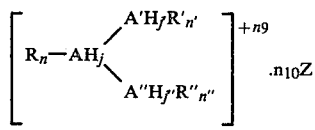
(B)

wherein:

R, R', R'', $R^1$, $R^2$, $R^3$, $R^4$, $R^5$ and $R^6$ are each independently selected from hydrogen; or substituted or unsubstituted alkyl, alkylene, aryl, alkylaryl, arylalkyl, monocycloalkyl, polycycloalkyl, heterocyclic and carbocyclic group; and R plus $R^i$ in formula (A) may be taken together to form a cyclic compound;

A, A', A'', $A^1$, $A^2$, $A^3$, $A^4$, $A^5$ and $A^6$ are independently neutral functional elements, each having a free electron pair available for accepting a proton to provide a charged ligand and having the capability of complexing with Tc-99m to form a cationic complex;

$Y^1$, $Y^2$, $Y^3$, $Y^4$, $Y^5$ and $Y^6$ are each independently selected from hydrogen; or substituted or unsubstituted alkyl, alkylene, aryl, alkylaryl, arylalkyl, monocycloalkyl, polycycloalkyl, heterocyclic and carbocyclic groups;

Z is an anion;

i is an integer from 0 to 6;

j, j' and j'' are each independently 0 or 1;

$k^1$, $k^2$, $k^3$, $k^4$, $k^5$ and $k^6$ are each independently 0 or 1;

n, n' and n'' are each independently the integer 1 or 2;

$n_1$, $n_2$, $n_3$, $n_4$, $n_5$, $n_6$, are independently 0 or 1;

$n_7$ and $n_8$ are each an integer from 1 to 6; and $n_9$ and $n_{10}$ are each an integer from 1 to 3.

2. An essentially aqueous solution of a cationic complex formed by complexing said compound of claim 1 with technetium.

3. An essentially aqueous solution of a cationic complex formed by complexing said compound of claim 1 with technetium in the presence of a halide or other suitable complex formation assisting anion.

4. An aqueous solution comprising the compound of claim 1.

5. The compound of claim 1 having the formula:

$$R(AH_jR'_{n'})_n{}^{+n}.n''Z$$

wherein R is ethyl or phenyl, A is phosporous or arsenic, and R' is a lower alkyl group having from 1 to about 6 carbon atoms.

6. The compound of claim 5 wherein Z is bisulfate, biphosphate, or tetrafluoroborate.

7. The compound of claim 1 wherein Z is derived from sulfuric acid, phosphoric acid, perchloric acid, nitric acid or boric acid.

8. The compound of claim 1 wherein A is selected from the group consisting of P, As, N, O, S, Sb, Se and Te.

9. The compound of claim 1 having the formula:

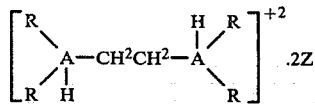

wherein

A is P or As; and each R is independently H, a lower alkyl group having from 1 to about 6 carbon atoms, or phenyl.

10. The compound of claim 9 wherein Z is bisulfate, biphosphate, nitrate, tetrafluoroborate or perchlorate.

11. An essentially aqueous solution of a cationic complex formed by complexing the compound of claim 9 with technetium.

12. An essentially aqueous solution of a cationic complex formed by complexing the compound of claim 9 with technetium in the presence of a halide or other suitable complex formation assisting anion.

13. The compound of claim 9 wherein A is phosphorus.

14. The compound of claim 9 wherein A is phosphorous and R is methyl or ethyl.

15. The compound of claim 9 having the formula:

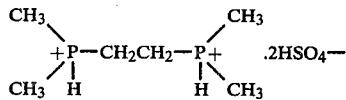

16. The compound of claim 1 having the formula:

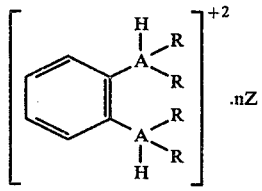

wherein A is P or As; and each R is independently H, or a lower alkyl group having from 1 to about 6 carbon atoms.

17. The compound of claim 16 wherein Z is bisulfate, biphosphate, nitrate, tetrafluoroborate or perchlorate.

18. An essentially aqueous solution of a cationic complex formed by complexing the compound of claim 15 or claim 16 with technetium.

19. An essentially aqueous solution of a cationic complex formed by complexing the compound of claim 15 or claim 16 with technetium in the presence of a halide or other suitable complex formation assisting anion.

20. The compound of claim 16 wherein A is phosphorous.

21. The compound of claim 16 wherein A is phosphorus and R is methyl or ethyl.

22. The compound of claim 16 having the formula:

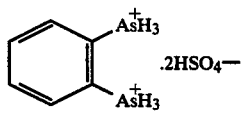

23. A kit for preparing a radiopharmaceutical preparation comprising a sealed, sterilized vial containing the compound of claim 1, 5, 6, 7, 8, 9, 10, 13, 14, 15, 16, 17, 20, 21, or 22.

24. The kit of claim 23 wherein said vial further contains a halide or other suitable complex formation assisting anion.

25. A method for making a cationic complex comprising Tc-99m for radioscintigraphic imaging, said method comprising admixing the compound of claim 1 with an essentially aqueous solution containing Tc-99m in the presence of a halide or other suitable complex formation assisting anion and heating the admixture to form a stable complex.

26. The method of claim 25 carried out under aseptic conditions and in a closed system.

27. The method of claim 26 wherein said compound is contained in a sterile, sealed vial and said solution is aseptically added to said vial.

28. The method of claim 25 wherein said compound is a solid, water-soluble salt of bis-1,2-(dimethylphosphino)ethane or o-phenylenebis(dimethylarsine), the halide is bromide or chloride, and the $^{99m}$Tc-containing solution comprises a physiological saline solution of $^{99m}$Tc-pertechnetate.

29. The method of claim 25 wherein said solution is substantially free of organic solvents.

30. The method of claim 25 wherein said solution further comprises ethanol or propylene glycol.

31. The method of claim 25 wherein said heating step is carried out at a temperature greater than 80° C.

32. The method of claim 25 wherein said heating step is carried out at a temperature greater than 100° C.

33. A method for visualizing the heart or the hepatobiliary system of a mammal by radioscintigraphy, and method comprising injecting into the mammal the cationic complex formed by the method of claim 25, and scanning the mammal using radioscintigraphic imaging apparatus.

34. The method of claim 25 wherein the pH is maintained in the range of from about 1.0 to about 3.0 during the admixing and heating steps.

35. The method of claim 25 wherein the pH is maintained in the range of from about 1.0 to about 3.0 during the heating step.

36. The method of claim 34 or claim 35 further comprising the step of adjusting the pH into the range of about 4.0 to about 9.0, injecting said complex into a mammal, and scanning the mammal using radioscintigraphic imaging apparatus.

* * * * *